US007037653B2

United States Patent
Benedí Benito et al.

(10) Patent No.: US 7,037,653 B2
(45) Date of Patent: May 2, 2006

(54) MOLECULAR METHODS FOR DETECTING GUAR GUM ADDITIONS TO LOCUST BEAN GUM

(75) Inventors: Vicente Javier Benedí Benito, Palma de Mallorca (ES); Antonio Doménech Sánchez, Palma de Malloraca (ES); María Luz Hernández Viadel, Valencia (ES); Sebastián Albertí Serrano, Palma de Mallor (ES); Josep Antoni Rosselló Picornell, Valencia (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 279 days.

(21) Appl. No.: 10/009,980

(22) PCT Filed: Mar. 2, 2001

(86) PCT No.: PCT/ES01/00079

§ 371 (c)(1),
(2), (4) Date: Sep. 10, 2002

(87) PCT Pub. No.: WO01/66794

PCT Pub. Date: Sep. 13, 2001

(65) Prior Publication Data

US 2004/0072155 A1    Apr. 15, 2004

(30) Foreign Application Priority Data

Mar. 8, 2000  (ES) ................................ 200000560

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........................ 435/6; 435/91.2; 536/23.1; 536/24.3

(58) Field of Classification Search .................... 435/6, 435/91.1, 91.2; 536/23.1; 436/20, 174, 436/175, 177
See application file for complete search history.

(56) References Cited

FOREIGN PATENT DOCUMENTS

WO    WO 98/14607    4/1998

OTHER PUBLICATIONS

Meyer, K. et al., "Determination of Locust Bean Gum and Guar Gum by Polymerase Chain Reaction and Restriction Fragment Length Polymorphism Analysis", J. AOAC Int., vol. 84, pp. 89-99 (Jan. 2001).*
Meyer, R. et al., "Polymerase Chain Reaction-Restriction Fragment Length Polymorphism Analysis: A Simple Method for Species Identification in Food", J. AOAC Int., vol. 78, pp. 1542-1551 (1995).*
Meer, W. A., Food Colloids, Graham, H.D. editor, The AVI Publishing Company, Inc., Westport, Connecticut, pp 522-539 (1977.*
Drake, M. et al., "Rapid Detection and Identification of Lactobacillus spp. in Dairy Products by Using the Polymerase Chain Reaction", J. Food protect., vol. 59, pp. 1031-1036 (1996).*
White, T. et al.: "Amplification and Direct Sequencing of Fungal Ribosomal RNA Genes for Phylogenetics," *PCR Protocols: A Guide to Methods and Applications*, Academic Press, Inc., San Diego. 1990, pp. 315-322.
Accession No. AF274687, EMBL/GenBank/DDBJ database, Barker, N.P., et al.: "Generic relationships in the tribe Indigoferae (Leguminosae: Papilionoideae) based on sequence data and morphology" Jun. 5, 2000.

(Continued)

*Primary Examiner*—Jeffrey Fredman
*Assistant Examiner*—Teresa Strzelecka
(74) *Attorney, Agent, or Firm*—Welsh & Katz, LTD

(57) ABSTRACT

The invention concerns methods for detecting guar gum alone or in mixtures of guar gum and locust bean gum. The invention also concerns methods for extracting, amplifying, and detecting DNA of guar and locust bean gums and the mixtures thereof. DNAs of plants from which guar and locust bean gums are extracted are amplified by means of polymerase chain reaction (PCR) using conserved initiators. Differences in the sequences of the amplification products obtained from these two plants enable their differentiation, the identification of guar DNA in mixtures of guar and locust bean gum mixtures and the design of guar-specific PCR initiators which detect guar only in mixtures of guar and locust bean gum.

7 Claims, 9 Drawing Sheets

OTHER PUBLICATIONS

Dlauchy, Denes et al., "Restriction Enzyme Analysis of PCR Amplified rDNA as a Taxonomic Tool in Yeast Identification." 1999 Syst. Appl. Microbiol. 22 (3), 445-453.

Dawkins, N.L. Studies on the extractability, structural and physicochemical properties or oat gum/beta. glucan. 1994 Dissertation International Abstract, 55 (4) 1241-B, No. DA9423975.

Panday, Ram Naresh et al., Inhibition of Random Amplified Polymorphic DNAs (RAPDs) by plant polysaccharides 1996 Plant Mol. Biol. Rep. 14(a), 17-22.

* cited by examiner

ITS5:   GGAAGTAAAAGTCGTAACAAGG
ITS3:   GCATCGATGAAGAACGCAGC
ITS4:   TCCTCCGCTTATTGATATGC
ITS2:   GCTGCGTTCTTCATCGATGC
PG21:   TCCAAAACAAGATGGAGTCG
PG22:   TGCCTGGGCGTCGCGCGTC

```
                ITS5
AJ245578    1  T|GGAAGGAGAAGTCGTAACAAGG|TTTCCGTAGGTGAACCTGCGGAAGGAT   50
AJ245575    1   TGGAAGGAGAAGTCGTAACAAGGTTTTCGTAGGTGAACCTGTGGAAGGAT   50
               ***********************  **************  *******

AJ245578   51  CATTGTCGATGCCTCACAAGCAGTCCGACCCGTGAACTTGTTTTGCTTAT  100
AJ245575   51  CATTGTCGATGCCTCACAAAACGAACGACCTGCGAATTGGTTAAACT-AT   99
               *******************   * ***** * *** * ***   ** **

AJ245578  101  TTAGGGTTGGTTTGGGGCGTGTCAAAACACGCCGACCTTCCTTTGGTTGG  150
AJ245575  100  CGGGGGCGGG--GGGCGTGCGTCCTCCCAAGCCTCCATGTCGGGAGGCGC  147
                 ***  **   ** * ***    ** ***   *   *     *    *

AJ245578  151  GAGTTGTCTGCCTTGCGTGGCTTTCTCTTAGCCTTTAACAAACCCACCGG  200
AJ245575  148  CTGTGGCCCCCCGCCACTCGTGCTACCTCGACCAAAAAACTAACC-CTGG  196
                 ** *  **    *  * ***  *  **  *  **  **  * ** **

AJ245578  201  CGCTACACGCGCCAAGGAAACTTAACTNTTCTGTGCGCCCTTGCCAGCCC  250
AJ245575  197  CGTTTAACGCGCCAAGGAACTACAACCAGTGAGCGTGCTCCCGATGACCT  246
               ** *  ************   ***    *   * * **  *    **

AJ245578  251  GGTAACGGTGCTGTGTAGGTT-GNGTTTAGATACATGAATC-AAAATGAC  298
AJ245575  247  GGTAACGGCGATCGATCGATGAGCGTCGTGACATTCTTATCCAAAATGAC  296
               ********  *    * *   * **   *    *   *   *******

AJ245578  299  TCTCGGCAACGGATATCTCGGCTCTCGCATCGATGAAGAACGCAGCA    345
AJ245575  297  TCTCGGTAACGGATATCTCGGCTCTC|GCATCGATGAAGAACGCAGC|A   343
               ******  *****************  ********************
                                                              ITS2
```

Figure 2

```
                        ITS3
AJ245577      1  T GCATCGATGAAGAACGCAGC GAAATGCGATACTTGGTGTGAATTGCAGA   50
AJ245576      1  TGCATCGATGAAGAACGCAGCGAAATGCAATACTTGGTGTGAATTGCAGA    50
                 *********************** *******************

AJ245577     51  ATCCCGCGAACCTTCGAGTCTTTGAACGCAAGTTGCGCCCGAAGCCATTA   100
AJ245576     51  ATCTTGTGAACCATCAAGTCTTTGAACACAAGTTGTGCCCGAAGCCATCA   100
                 ***  * *****  ** ********** ****** ************ *
                                    PG22
AJ245577    101  GGCCGAGGGCACGCC TGCCTGGGCGTCGCGCGTC GTTGCCCTAACTCGG-  149
AJ245576    101  AGCCGAAGGCACGTCTGCCTGGGTGTCACACACTGTCGCCCCCACCCCGT   150
                  ***** ****** *********  *** * *   ** ****  ** * *

AJ245577    150  -ACGTCTCATTTGGTGTCGTTGAGTGG-CGAATGTTGGCTTCCCACGAGC   197
AJ245576    151  GGCCTCTCGCGTGGCTTCGAGGAATGGGCAGATTATGGCCTTCCGTGAGC   200
                   * ****   ***   ***   ** *** *  **** ****  ****

AJ245577    198  GTTGCCTCATGGTTGGTTGAAATTCGAGTCCGTGGTGGAGGATGCCACGA   247
AJ245576    201  TTCGCCTTATGGATGGCCCAAAAGAGAGTTCGCGGTGGCGACTGCCACGA   250
                  * **** **** ***   *** *****  ** ***** *  *******
                                                                  PG21
AJ245577    248  TTGATATGGTGGTTGAGTAATTAGCTCGAGACCCATCGTGAG CGACTC-C    296
AJ245576    251  C--GCACGGTGGATGAGCAAAGA-CTCAAGACCAGTCGTGCAAGTGTCAT   297
                  *  ***** ***  * *** *****  *****  *   * **
                       PG21
AJ245577    297  ATCTTGTTTTGGA CTCTTTGACCC----ACATGAGCATCTCCG-ATGCTC   341
AJ245576    298  ACCCGGGATTGCGCTCGGAGACCCCTTCAGCATCGCGAGGTGCATATGCCT   347
                 *  *   *   ***  ***  *****     ***  *  *   ****

AJ245577    342  GTTACGAGACCTCAGGTCAGACGGGGTTACCCGCTGAGTTTAA GCATATC   391
AJ245576    348  CGAACGGGACCCTAAGTCAGGCGGGGCTACTCGCTGAGTTTAAGCATATC   397
                  ** ****  *  *****  *** ***  *********************
                                                              ITS4
AJ245577    392  AATAAGCGGAGGA A  405
AJ245576    398  AATAAGCGGAGGA    410
                 *************
                       ITS4
```

Figure 3

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of the Artificial Sequence:oligo
      ITS5

<400> SEQUENCE: 1
ggaagtaaaa gtcgtaacaa gg                                              22

<210> SEQ ID NO 2
<211> LENGTH: 20
<212> TYPE: DNA
<213> ORGANISM: Artificial Sequence
<220> FEATURE:
<223> OTHER INFORMATION: Description of the Artificial Sequence:oligo
      ITS3

<400> SEQUENCE: 2
gcatcgatga agaacgcagc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of the Artificial Sequence:oligo
      ITS4

<400> SEQUENCE: 3
tcctccgctt attgatatgc                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of the Artificial Sequence:oligo
      PG21

-continued

```
<400> SEQUENCE: 4
gctgcgttct tcatcgatgc                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of the Artificial Sequence:oligo
      ITS2

<400> SEQUENCE: 5
tccaaaacaa gatggagtcg                                                    20

<210> SEQ ID NO 6
<211> LENGTH: 19
<212> TYPE: DNA
<213> ORGANISM: Artificial Sequence
<220> FEATURE:
<223> OTHER INFORMATION: Description of the Artificial Sequence:oligo
      PG22

<400> SEQUENCE: 6
tgcctgggcg tcgcgcgtc                                                     19

<210> SEQ ID NO 7
<211> LENGTH: 345
<212> TYPE: DNA
<213> ORGANISM: Cyamopsis tetragonoloba
<220> FEATURE:
<221> NAME/KEY: primer_bind
<222> LOCATION: Complement((2)..(23))
<220> FEATURE:
<221> NAME/KEY: SITE
<222> LOCATION: (228)
<223> OTHER INFORMATION: n=a, c, g or t
<220> FEATURE:
<221> NAME/KEY: SITE
<222> LOCATION: (273)
<223> OTHER INFORMATION: n=a, c, g or t
<220> FEATURE:
<221> NAME/KEY: primer_bind
<222> LOCATION: (325)..(344)

<400> SEQUENCE: 7
tggaaggaga agtcgtaaca aggttttccgt aggtgaacct gcggaaggat cattgtcgat       60
gcctcacaag cagtccgacc cgtgaacttg ttttgcttat ttagggttgg tttgggcgt       120 gtcaaaacac gccgaccttc ctttggttgg gagttgtctg ccttgcgtgg cttttctctta     180 gcctttaaca aacccaccgg cgctacacgc gccaaggaaa cttaactntt ctgtgcgccc     240
ttgccagccc ggtaacggtg ctgtgtaggt tgngtttaga tacatgaatc aaaatgactc     300
tcggcaacgg atatctcggc tctcgcatcg atgaagaacg cagca                      345

<210> SEQ ID NO 8
<211> LENGTH: 343
<212> TYPE: DNA
<213> ORGANISM: Ceratonia siliquia
<220> FEATURE:
<221> NAME/KEY: primer_bind
<222> LOCATION: (2)..(23)
<220> FEATURE:
<221> NAME/KEY: primer_bind
<222> LOCATION: Complement((323)..(342))

<400> SEQUENCE: 8
tggaaggaga agtcgtaaca aggttttcgt aggtgaacct gtggaaggat cattgtcgat       60
```

-continued

```
gcctcacaaa acgaacgacc tgcgaattgg ttaaactatc gggggcgggg ggcgtgcgtc      120
ctcccaagcc tccatgtcgg gaggcgcctg tggccccccg ccactcgtgc tacctcgacc      180
aaaaaactaa ccctggcgtt taacgcgcca aggaactaca accagtgagc gtgctcccga      240
tgacctggta acggcgatcg atcgatgagc gtcgtgacat tcttatccaa aatgactctc      300
ggtaacggat atctcggctc tcgcatcgat gaagaacgca gca                        343
```

<210> SEQ ID NO 9
<211> LENGTH: 405
<212> TYPE: DNA
<213> ORGANISM: Cyamopsis tetragonoloba
<220> FEATURE:
<221> NAME/KEY: primer_bind
<222> LOCATION: Complement((2)..(21))
<220> FEATURE:
<221> NAME/KEY: primer_bind
<222> LOCATION: (385)..(404)

<400> SEQUENCE: 9

```
tgcatcgatg aagaacgcag cgaaatgcga tacttggtgt gaattgcaga atcccgcgaa      60
ccttcgagtc tttgaacgca agttgcgccc gaagccatta ggccgagggc acgcctgcct     120
gggcgtcgcg cgtcgttgcc ctaactcgga cgtctcattt ggtgtcgttg agtggcgaat     180
gttggcttcc cacgagcgtt gcctcatggt tggttgaaat tcgagtccgt ggtggaggat     240
gccacgattg atatggtggt tgagtaatta gctcgagacc catcgtgagc gactccatct     300
tgttttggac tctttgaccc acatgagcat ctccgatgct cgttacgaga cctcaggtca     360
gacggggtta cccgctgagt ttaagcatat caataagcgg aggaa                      405
```

<210> SEQ ID NO 10
<211> LENGTH: 410
<212> TYPE: DNA
<213> ORGANISM: Ceratonia siliqua
<220> FEATURE:
<221> NAME/KEY: primer_bind
<222> LOCATION: (2)..(23)
<220> FEATURE:
<221> NAME/KEY: primer_bind
<222> LOCATION: Complement((385)..(404))

<400> SEQUENCE: 10

```
tgcatcgatg aagaacgcag cgaaatgcaa tacttggtgt gaattgcaga atcttgtgaa      60
ccatcaagtc tttgaacaca agttgtgccc gaagccatca agccgaaggc acgtctgcct     120
gggtgtcaca cactgtcgcc cccacccgt ggcctctcgc gtggcttcga ggaatgggca      180
gattatggcc ttccgtgagc ttcgccttat ggatggccca aaagagagtt cgcggtggcg     240
actgccacga cgcacggtgg atgagcaaag actcaagacc agtcgtgcaa gtgtcatacc     300
cgggattgcg ctcggagacc cttcagcatc gcgaggtgca tatgcctcga acgggaccct     360
aagtcaggcg gggctactcg ctgagtttaa gcatatcaat aagcggagga               410
```

MOLECULAR METHODS FOR DETECTING GUAR GUM ADDITIONS TO LOCUST BEAN GUM

TECHNICAL FIELD

Locust bean gum, synonym of algaroba gum and carob bean gum, extracted from the seeds of carob trees (*Ceratonia siliqua*), and guar gum, synonym of gum cyamopsis and guar flour, extracted from the seeds of guar plant (*cyamopsis tetragonolobus*) are used as food additives. They are mainly used as thickening, emulsifying, stabilizing, or gelling agents in the food industry. As described in the Official Journal of the European Communities from 9.12.98, pages L334/11 through L334/13, locust bean gum is coded as additive E 410 and guar gum has the code E 412, and these code numbers will be used in the present as synonyms of the above gums. As food additives, E 410 and E 412 can be used alone or together, or even combined with other additives such as carrageenan (E 407), xanthan (E 415) and pectin (E 440i). The addition of these additives to foods provide general effects such as body, smoothness, and chewiness. Examples of these additions and of the effects they provide are: delaying the melting of ice creams, reduction of solids loss and speeding of curd formation in soft cheese manufacturing, and binding in composite meat products such as salami and sausages. Besides these food products, jams and jellies, milk products, breakfast cereals, soups and soup mixes, sauces, gravies, toppings and syrups, and other food categories, may have additions of either or both E 410 and E 412 up to maximum usage levels permitted of between 0.15% and 2.0%, depending on the food category and on the additive.

BACKGROUND ART

As described in the *Official Journal of the European Communities* [1998, "Commission Directive 98/86/EC of 11 Nov. 1998," *Official Journal of the European Communities* 9.12.98:L334/11], E 410 and E 412 can be differentiated by microscopic examination of their aqueous solutions stained with iodine and potassium iodide. In such preparations, E 410 presents long stretched tubiform cells, separated or slightly interspaced. Their brown contents are much less regularly formed in guar gum than in locust bean gum. E 412 shows close groups of round to pear shaped cells. Their contents are yellow to brown. Thus, theoretically, this microscopy methods should allow identification of guar in mixtures of of guar gum and locust bean gum.

E 410 and E 412, individually or mixed, can be added as food additives, provided that the food label indicates whether only one of these two or a combination of the two additives is present. Both E 410 and E 412 are galactomannans and differences in their chemical composition have been described: galatose:mannose ratios of 1:4 and 1:2, in locust bean gum and guar gum, respectively. Thus, isolated E 410 and E 412 can easily be differentiated from each other by gas-liquid chromatography of the hydrolyzed and derivatized polysaccharides, and after calculation of the galactose:mannose ratio in the resulting chromatogram. However, for these two polysaccharides, and depending of their origin, supplier, and batch, variations in the degree of substitution of the mannan main chain have been described. For example, 37% in E 412 and 23% in E 410 [Cheetham, N. W. H., B. V. McCleary, G. Teng, F. Lum, and Maryanto, 1986, "Gel-permeation studies on xanthan-galactomannan interactions," *Carbohydr. Polym.* 6:257-268], galactose:mannose ratios for E 410 and E 412 of 1:2.69 and 1:1.44, respectively [Angelini, E., C. Boniglia, M. Mosca, and G. Bellomonte, 1984, "Detection and determination of plant gums by gas-chromatographic determination of their constituent monosaccharides," *Rivista delta Societa Italiana di Scienza dell'Alimentazione*, 13:479–484], or 3.01:1 and 1.48:1, respectively [Preuss, A., and H. P. Their, 1982, "Quantitative analysis of natural thickeners and gums by methanolysis and capillary column gas chromatography," *Z. Lebensm. Unters. Forsch.* 175:93–100]. Even galactose:mannose ratios ranging from 3.1:1 to 7.7:1 were determined in locust bean gum fractions solubilized at temperatures between 20° C. and 80° C. [Lopes da Silva, J. A., and M. P. Goncalves, 1990, "Studies on a purification method for locust bean gum by precipitation with ethanol," *Food Hydrocolloids*, 4:277–287]. Due to these variations in composition it may be technically impossible in some mixtures of E 410 and E 412 to ascertain the individual content of each gum, and, for the same reasons, a possible adulteration of E 410 with E 412 may be technically very difficult to demonstrate. Cases of adulteration of E 410 with E 412 have been documented. The interest of this type of adulterations can be deduced from the different prizes of the two additives, with E 412 being cheaper than E 410.

Polysaccharides of plant origin are widely used as stabilizing agents in the food industry, and thus many chemical and some physical methods have been used to identify and quantitate these agents in mixtures and foods. None of these methods reviewed by Morley et al. [Morley, R. G., G. O. Phillips, and D. M. Power, 1972, "Fractionation and identification of commercial hydrocolloid stabilising agents," *Analyst*, 97:315–319] neither the sequential fractionation scheme described in the cited reference can distinguish E 410 and E 412. More recently, the techniques generally used to identify and quantitate food additives of polysaccharide nature, the same general type of E 410 and E 412, including electrophoresis, gas chromatography and gas-liquid chromatography. None of these methods differentiate E 410 and E 412. Limitations of these methods, particularly when applied to the analysis of foods, are the need of complex extraction prior to analysis and expensive equipment. Furthermore, hydrolysis, the first necessary step for chromatographic analysis of a mixture of E 410 and E 412, will also release, for example, mannose from xanthan, thus affecting the galactose:mannose ratio. Xanthan is another food additive (E 415) which is often used in combination with E 410 and E 412.

In a different described method, E 410, E 412, and other polysaccharides used as food thickeners were isolated, pyrolised, and their products of pyrolysis were analyzed by gas chromatography. Although it was possible to identify a single food thickener by retention index monitoring and selected ion monitoring of the pyrolytic products, accurate analysis of a mixture of food thickeners was not achieved [Sjoeberg, A. M., and H. Pyysalo, 1985, "Identification of food thickeners by monitoring of their pyrolytic products," *J. Chromatography*, 319:90–98.].

An assay using the *Bandeiraea simplicifolia* lectin which allows detection/quantification of guar and locust bean gum in commercial food products has been described [Patel, P. D., and G. B. Hawes, 1988, "Estimation of food-grade galactomannans by enzyme-linked lectin assay," *Food Hydrocolloids*, 2:107–118]. Although the referred method detected E 410 and E 412 and not other food additives of polysaccharide nature (xanthan, carrageenan, alginates, and pectin), guar and locust bean gums could not be differentiated.

Finally, DNA-based methods have been described for the detection and/or identification of plants and plant-derived products. For example, in patent WO/9814607, a method is described for detecting a particular plant species in foodstuffs. The method is based in the detection of plant-specific sequences located in the chloroplast DNA. Regions of the chloroplast DNA that contain characteristic sequences of some example plants were identified in the cited patent, allowing the differentiation between oranges and mandarines. Although the methods described in the patent may be applicable to the differentiation of plant species other than those these described in the examples of this patent, these methods were not applied to the differentiation of either guar plant and carob tree neither to their derived products E 410 and E 412, respectively. On the other hand, there are reports of sometimes insufficient phylogenetic resolution in studies based on chloroplastic DNA, i.e., that they do not always allow species identification [Baldwin, B. G., M. J. Sanderson, J. M. Porter, M. F. Wojciechowski, C. S. Campbell, and M. J. Donoghue, 1995, "The ITS region of nuclear ribosomal DNA: a valuable source of evidence on angiosperm phylogeny," *Ann. Missouri Bot. Garden.* 82:247–277]. Additionally, as of today, there are not chloroplastic sequences available for the guar plant, and its differentiation from carob tree and other plant species based on these DNA sequences would require first their identification, isolation and sequencing. Finally, for the reasons detailed below, the extraction of DNA, either chlorplastic or not, from thickening agents, may require special methods that are not described in the cited patent.

For the present patent, it is finally relevant the description of a DNA based-method for the detection of wheat contamination in 35 samples of foods and food additives [Allmann, M., U. Candrian, C. Höfelein, and J. Lüthy, 1993, "Polymerase chain reaction (PCR): a possible alternative to immunochemical methods assuring safety and quality of food: Detection of wheat contamination in non-wheat food products," *Z. Lebensm. Unters. Forsch.* 196:248–251]. This method is based on the use of PCR and primers specific for the ribosomal DNA, i.e., on sequences of wheat DNA encoding for the RNA components of the ribosomes. It is important for the present patent to note that the authors of the cited method concluded that thickening agents or additives, in particular guar gum and locust bean gum, could not serve as a substrates for DNA isolation, and that the thickening and absorption effects of these additives made DNA extraction impossible.

BRIEF DESCRIPTION OF THE INVENTION

We describe the existence of diagnostic DNA sequences that allow identification of the plants from which guar and locust bean gums are extracted. These sequences have also been detected in the guar and locust bean gums, thus their detection in the DNA extracted from these gums ensure that their origins are either the guar plant or the carob tree.

Using PCR and the conserved primers (initiators) described in FIG. 1A, we have amplified two DNA regions named ITS1 and ITS2 from the DNA extracted from the seeds of *Ceratonia siliqua* and *Cyamopsis tetragonolobus*, i.e., the plants from which the locust bean gum (E 410) and guar gum (E 412) are extracted. Analysis of the amplification products with restriction endonucleases showed restriction patterns specific of each. Direct DNA sequencing and comparison of the aligned sequences showed that both plants can be differentiated by the presence of nucleotides specific of each plant species found in certain positions of the sequence. Furthermore, scrutiny for conserved and variable nucleotides within these sequences indicated the existence of two regions in the DNA amplified from the guar plant, that we name PG21 (SEQ ID NO:5) and PG22 (SEQ ID NO:6), whose sequences can be used as primers for the specific amplification by PCR of a region of guar DNA within the ITS2 region. Sequences and positions of these primers specific of guar are shown in FIGS. 1A and 3. Once the specific primers PG21 (SEQ ID NO:4) and PG22 (SEQ ID NO:6) were tested for amplification of DNA extracted not from seeds but from commercial preparations of locust bean gum (E 410) and guar gum (E 412) we concluded that the usual methods described in the literature to extract DNA do not allow PCR amplification from these samples. Thus, we developed alternative methods for the extraction of DNA from these gums, which allowed DNA amplification. Using primers PG21 (SEQ ID NO:4) and PG22 (SEQ ID NO:6), we obtained amplification by PCR from the DNA extracted of all known samples of guar gum, and no amplification from any of control samples of locust bean gum. Furthermore, we demonstrate that with these DNA extraction and amplification methods we have detected guar DNA both in known control mixtures of guar and locust bean gum and in some commercial preparations labeled as "locust bean gum" which, theoretically, should not contain guar.

DETAILED DESCRIPTION OF THE INVENTION AND EXAMPLES

As used herein, the term locust bean gum or E 410 is the ground endosperm of the seeds of the natural strains of carob tree *Ceratonia siliqua* [1998, "Commission Directive 98/86/EC of 11 Nov. 1998," *Official Journal of the European Communities,* 9.12.98:L334/11]. The term guar gum or E 412, as used herein, is the ground endosperm of the seeds of natural strains of the guar plant [1998, "Commission Directive 98/86/EC of 11 Nov. 1998," *Official Journal of the European Communities,* 9.12.98:L334/11]. For a detailed description of both terms we conform to what is described in the reference [1998, "Commission Directive 98/86/EC of 11 Nov. 1998," *Official Journal of the European Communities,* 9.12.98:L334/11]. Although this invention does not claim taxonomical issues, some of the sequences described here as part of the claims may have taxonomical applications. Thus, the taxonomical status of carob tree and guar plant species requires further explanation. For example, in reference [1998, "Commission Directive 98/86/EC of 11 Nov. 1998," *Official Journal of the European Communities,* 9.12.98:L334/11] both plant species are considered as belonging to the family Leguminosae, whereas other taxonomical sources, such as the National Center for Biotechnology Information (NCBI) (http://www.ncbi.nlm.nih.gov/Taxonomy/tax.html) prefers to use the family name Fabaceae. We consider herein both family names as synonyms, in accordance with considerations of the International Code of Botanical Nomenclature (Tokyo Code, Koeltz Scientific Books, Germany, 1994). Another taxonomical issue refers to the scientific name of the guar plant, cited as *Cyamopsis tetragonolobus* in reference [1998, "Commission Directive 98/86/EC of 11 Nov. 1998," *Official Journal of the European Communities,* 9.12.98:L334/11] or as *Cyamopsis tetragonoloba* by the NCBI taxonomy database. Again, we will consider herein both species names as synonyms of the guar plant.

The terms DNA, PCR, primers, and sequences, are common for those skilled in the molecular biology field. We would refer to them herein as follows. DNA refers to deoxyribonucleic acid. PCR refers to methods for in vitro amplification of DNA where two synthetic oligonucleotide primers, which are complementary to two regions of the target DNA (one for each strand) to be amplified, are added to the target DNA, in the presence of excess deoxynucleotides and a heat-stable polymerase (Taq polymerase). In a series (typically 30) of temperature cycles, the target DNA is repeatedly denatured, annealed to the primers, and a daughter strand extended from the primers. The daughter strands themselves (sometimes referred as amplicons) act as templates for subsequent cycles, where DNA fragments matching both primers are amplified exponentially. Primer, or initiator, refer to a short pre-existing polynucleotide chain to which new deoxyribonucleotides can be added during the PCR process. Primers PG21 (SEQ ID NO:5) and PG22 (SEQ ID NO:6) have been produced synthetically, and are of sufficient length and with sequences that ensure that they recognize and anneal to specific DNA sequences within the ITS2 region of the genome of the guar plant and they do not anneal to the carob tree genome. DNA sequences refer to the relative order of DNA bases or nucleotides (A, C, T, G), whether in a fragment of DNA, a gene, a chromosome, or an entire genome.

The regions known as "internal transcribed spacer" or ITS are constituents of the 18S–26S nuclear ribosomal DNA (rDNA), which encodes for the RNA component of the ribosomes (rRNA). The ITS are useful for phylogenetic studies of angiosperm plants [Baldwin, B. G., M. J. Sanderson, J. M. Porter, M. F. Wojciechowski, C. S. Campbell, and M. J. Donoghue, 1995, "The ITS region of nuclear ribosomal DNA: a valuable source of evidence on angiosperm phylogeny," *Ann. Missouri Bot. Garden.* 82:247–277]. The organization of these regions in the plant genomes is as shown in FIG. 1A: two ITS regions named ITS1 and ITS2 are separated by a conserved small region named 5.8S and flanked by the 18S and 26S regions. Whereas ITS1 and ITS2 are highly variable in sequence within different families and genera of plants, the 5.8S, 18S, and 26S regions are highly conserved. The small size of the ITS regions (less than 300 nucleotides) and the fact that they are flanked by conserved sequences, facilitate their amplification by PCR with conserved oligonucleotide primers designed against the conserved flanking regions. The ITS regions, as well as the other components of the rDNA, are multiple copies in the plant genomes and this facilitates isolation, detection, amplification, cloning, and sequencing, even from old samples like herbarium material. Variations in length (number of nucleotides) between ITS regions of plants, although limited, have been described, and in some cases serve to differentiate between two close species. But most importantly for the present patent, differences in the sequence in the ITS regions usually allows differentiation between species of the same genus.

The present invention describes methods for the identification of guar gum, alone and in mixtures of guar gum and locust bean gum, by means of DNA amplification and its related analysis methods. For this purposes, we use rDNA sequences of the 18S, 5.8S, 26S, ITS1, and ITS2 regions described in reference [Baldwin, B. G., M. J. Sanderson, J. M. Porter, M. F. Wojciechowski, C. S. Campbell, and M. J. Donoghue, 1995, "The ITS region of nuclear ribosomal DNA: a valuable source of evidence on angiosperm phylogeny," *Ann. Missouri Bot. Garden.*, 82:247–277]. and in FIG. 1A. Since these regions were previously unknown for the guar plant and carob tree, the first experiments of this invention were addressed to determine the sequences of the ITS1 and ITS2 regions in the genomes of these two plant species.

For these purpose, we isolated DNAs from the seeds of the guar plant and carob tree, and amplified them by PCR using the primer pairs ITS5/ITS2 (SEQ ID NO:1/SEQ ID NO:4) and ITS3/ITS4 (SEQ ID NO:2/SEQ ID NO:3) described in [White, T. J., T. Bruns, S. Lee, and J. Taylor, 1990, "Amplification and direct sequencing of fungal ribosomal RNA genes for phylogenetics," in M. A. Innis, D. H. Gelfand, J. J. Sninsky, and T. J. White (ed.), *PCR Protocols: A Guide to Methods and Applications*, Academic Press, Inc., San Diego]. These pairs of primers amplify respectively the ITS1 and ITS2 and part of their adjacent regions (see FIG. 1A). The amplification products were directly sequenced or detected by electrophoresis in agarose gels, purified, cloned and sequenced. The resulting sequences were aligned using a computer program and the ITS1 and ITS2 regions and their boundaries were identified. Identification was performed by comparison of the sequences obtained with other known sequences of plant rDNA. The procedures and corresponding results are described in detail in the experiments shown in Example I.

Analysis of the sequences obtained from guar and carob tree seeds demonstrated that both amplicons containing ITS1 and ITS2 differ in their compositions and sequences, depending on the plant species. Analysis of these sequences by restriction with endonucleases (restriction enzymes or restrictases) can be performed with computer programs, like MacVector (Oxford Molecular Group PLC), in order to predict the sizes of the fragments that could be generated with each endonuclease. We performed these analysis on the computer (data not shown) and selected some restrictases to illustrate the usefulness of this type of analysis as a method to differentiate the DNA from both plant species. For these purpose, we first amplified separately the ITS1 and ITS2 containing regions from DNA extracted from the seeds of guar plant and carob tree, as detailed in Example I. Amplification products were purified and digested with several restrictases that produced differential restriction patterns for guar plant and carob tree. The results of this type of analysis, and the corresponding experimental details, are shown in Example II.

Differences in the DNA sequences obtained from the DNA extracted the seeds of guar and carob tree suggested that a method based on PCR and on these sequences could be designed for the specific detection of guar. The detailed study of the sequences from the two plants (shown in FIGS. 2 and 3) showed regions where the differences between the sequences of the two plants were most prominent. As a non-limiting example of this strategy, we selected the regions labeled as PG21 and PG22 in FIG. 3, and used them as guar specific primers for PCR. In these two regions, the sequences of the two plants differ in many nucleotides, particularly in the 3' regions of the indicated primers. It is well known in the field of PCR and molecular biology that differences in the sequence of the 3' regions of PCR primers, rather that in the 5' end, increase the specificity of PCR primers. As detailed in Example III, DNA extracted from seeds of guar plant was amplified with primers PG21/PG22, but no amplification was obtained for DNA extracted from seeds of carob tree. These demonstrated the specificity of the primers designed by us.

As mentioned before in this patent, PCR amplification of DNA from plants and other polysaccharide-rich environments is not always an easy task, because polysaccharides are good inhibitors of most enzymes used in molecular biology, such as polymerases, restrictases, and ligases [Michaels, S. D., M. C. John, and R. M. Amasino, 1994, "Removal of polysaccharides from plant DNA by ethanol precipitation," *Biotechniques,* 17:274–276]. This is exactly the situation one will find if a DNA-based method has to be devised for the detection of DNA in commercial preparations of guar and locust bean gums, because, by definition [1998, "Commission Directive 98/86/EC of 11 Nov. 1998," *Official Journal of the European Communities,* 9.12.98: L334/11], these samples must contain at least 75% polysaccharide (galactomannan). As an important number of methods and even commercial kits have been developed to overcome the problems caused by polysaccharides in DNA extraction and amplification, we tried several of these methods. We first tried the CTAB method [Doyle, J., and J. J. Doyle, 1987, "A rapid DNA isolation procedure for small quantities of fresh leaf tissue," *Phytochem. Bull.* 19:11–15] used with success in this invention to extract DNA from seeds (see Example I). We also assayed an SDS-based method [Milligan, B. G. 1994, "Plant DNA isolation", p. 59–98, in A. R. Hoelzel (ed.), *Molecular Genetic Analysis of Populations: A practical approach*, Oxford University Press, Oxford], an ethanol-based method [Michaels, S. D., M. C. John, and R. M. Amasino 1994 "Removal of polysaccharides from plant DNA by ethanol precipitation," *Biotechniques'* 17:274–276.], and the commercial kits Nucleon PhytoPure Plant DNA extraction kit (Amersham Life Science) and DNeasy Plant kit (Qiagen). We did not obtain DNA amplification by PCR from commercial samples of guar gum, locust bean gum, or from mixtures of guar and locust bean gum (data not shown) with none of these methods. These negative results were reported before by authors who could not obtain amplifications from guar and locust bean gums, whereas they obtained amplifications from other plant-derived materials and foods using the same experimental conditions [Allmann, M., U. Candrian, C. Höfelein, and J. Lüthy 1993 "Polymerase chain reaction (PCR): a possible alternative to immunochemical methods assuring safety and quality of food: Detection of wheat contamination in non-wheat food products," *Z. Lebensm. Unters. Forsch.* 196:248–251]. These authors, when referring to the negative results obtained for guar and locust bean gums, concluded that " . . . the thickening and absorption effects made any extraction impossible . . . " of the DNA. Since none of the above mentioned methods produced positive results, we decided to investigate and develop our own methods for DNA extraction from locust bean and guar gums.

For these purpose, locust bean and guar gum (0.1–10%, w/w) and mixtures of these gums with known percent contents of each gum were suspended in either water ("water method"), buffers with different ionic strengths and compositions ("Tris method"), acetonitrile solutions of different compositions ("acetonitrile method"), or ethanol solutions ("ethanol method") at temperatures ranging from 4° C. to 65° C. Suspensions were vortexed between 1 and 10 min and centrifuged. The supernatant fluids were recovered and used for PCR and for DNA and polysaccharide quantitations. In the ethanol method, the procedure described in the reference [Michaels, S. D., M. C. John, and R. M. Amasino, 1994, "Removal of polysaccharides from plant DNA by ethanol precipitation," *Biotechniques* 17:274–276] was followed, and at the end of the cited procedure, the dissolved material was used for the same PCR and quantitations used with the other extraction methods. For PCR amplification, the PG21/PG22 primers pair and the conditions described in Example III were used. The results obtained with these extraction methods are summarized in Table 1 and detailed in Example IV.

As explained in detail in example IV, although the water method extracts less DNA than the Tris method (the method that extracts more DNA for each gum or mixture assayed), the water method is the most adequate method of DNA extraction for its subsequent PCR amplification. For these reasons, the water method was selected for future PCR experiments.

The usefulness of the methods described in this patent for the extraction and amplification of DNA from guar and locust bean gums and their mixtures was further verified by testing laboratory preparations of locust bean gum containing different known amount of guar gum, and by testing commercial preparations of locust bean gum. For these assays, the water method of DNA extraction and the PCR method with the PG21/PG22 primers were used. Analysis of the PCR products by direct electrophoresis or restriction analysis (see Example V for details) demonstrated that the methods described in this patent detect the presence of guar gum in mixtures of locust bean plus guar gum. It also demonstrates that among the commercial preparations labeled as "locust bean gum" analyzed, some of them contained guar gum.

The methods described in this patent rely on DNA sequences that are specific (diagnostic) of the guar plant and carob tree. Given their specificity, these DNA-based methods ensure the compliance with the legislative requirements of E 410 and E 412 as galactomannans extracted from the seeds of the species *Ceratonia siliqua* and *Cyamopsis tetragonolobus*, respectively [European, C. 1998, "Commission Directive 98/86/EC of 11 Nov. 1998," *Official Journal of the European Communities,* 9.12.98:L334/11]. Consequently, an additional result of the methods described here is that they confirm the authenticity of the locust bean gum and guar gums received from suppliers.

BRIEF DESCRIPTION OF THE DRAWINGS

FIG. 2 shows the sequences of the products shown on lanes 1 and 2 of FIG. 1B, i.e., ITS1 containing regions of guar plant and carob tree. Products were sequenced using the ITS5 and ITS2 primers (boxed in the figure). Sequence names (identifiers) correspond to EMBL/GenBank/DDBJ DNA accession numbers. Sequence identifier AJ245575 (SEQ ID NO:8) corresponds to carob tree, and sequence identifier AJ245578 (SEQ ID NO:7) corresponds to guar. Sequences were aligned using the MacVector program, and dashes correspond to sequence gaps automatically introduced by the program to improve the alignment, whereas asterisks indicate nucleotide positions conserved in the two sequences. The ITS1 region (underlined) was determined by comparison to published sequences of several angiosperm plants [Hershkovitz, M. A., and E. A. Zimmer, 1996, "Conservation patterns in angiosperm rDNA ITS2 sequences," *Nucleic Acids Research*, 24:2857–2876].

FIG. 3 shows the sequences of the products shown on lanes 3 and 4 of FIG. 1B, i.e., ITS2 containing regions of guar plant and carob tree. Products were sequenced using the ITS3 and ITS4 primers (boxed in the figure). Sequence identifiers are accession numbers of the EMBL/GenBank/DDBJ DNA databases. Sequence identifier AJ245576 (SEQ ID NO:10) corresponds to carob tree, and sequence identifier AJ245577 (SEQ ID NO:9) corresponds to guar. Sequences were aligned using the MacVector program, and dashes correspond to sequence gaps, whereas asterisks indicate conserved nucleotide positions. The ITS2 region (underlined) was defined by comparison to published sequences of several angiosperm plants [Hershkovitz, M. A., and E. A. Zimmer, 1996, "Conservation patterns in angiosperm rDNA ITS2 sequences," *Nucleic Acids Research*, 24:2857–2876]. The sequences of primers PG21 (SEQ ID NO:4) and PG22 (SEQ ID NO:6) designed in this patent are also shown.

EXAMPLE I

Figure 1A:
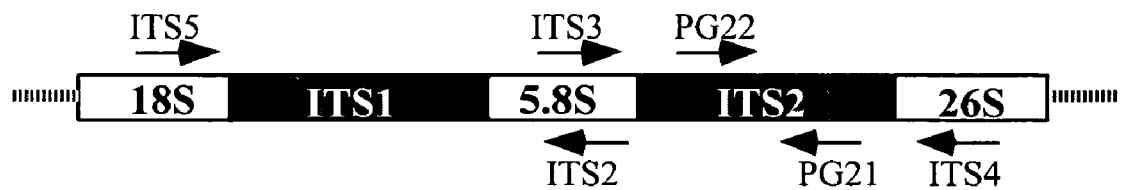
FIG. 1A shows the organization of the 18S–26S rDNA region. The relative positions of PCR primers used for the amplification of ITS1 and ITS2 containing regions, respectively the primer pairs ITS5 (SEQ ID NO:1)/ITS2 (SEQ ID NO:5) and ITS3 (SEQ ID NO:2)/ITS4 (SEQ ID NO:3), are shown. It also shows the position of the primers pair PG21 (SEQ ID NO:4)/PG22 (SEQ ID NO:6) used for the specific amplification of an internal region of the ITS2-containing region of guar. Sequences of primers ITS5 (SEQ ID NO:1), ITS2 (SEQ ID NO:5), ITS3 (SEQ ID NO:2), and ITS4 (SEQ ID NO:3) have been described in [White, T. J., T. Bruns, S. Lee, and J. Taylor, 1990, "Amplification and direct sequencing of fungal ribosomal RNA genes for phylogenetics," in M. A. Innis, D. H. Gelfand, J. J. Sninsky, and T. J. White (ed.), *PCR Protocols. A Guide to Methods and Applications*, Academic Press, Inc., San Diego].

Amplifications and Sequences of the ITS1 and ITS2 of the DNA Extracted from the Seeds of Guar Plant and Carob Tree Seeds of guar plant and carob tree were mechanically scarified, embedded in sterile water overnight and germinated on moist filter paper in Petri dishes. Total DNA was extracted from 20 mg of plant tissue using the CTAB protocol described in the reference [Doyle, J., and J. J. Doyle, 1987, "A rapid DNA isolation procedure for small quantities of fresh leaf tissue," *Phytochem. Bull.*, 19:11–15]. The DNA content of each sample was quantitated in a fluorimeter using the PicoGreen$^R$ dsDNA Quantitation Kit of Molecular Probes. Regions of the rDNA including the ITS1 and ITS2 were independently amplified by PCR using the primer pairs ITS5/ITS2 and ITS3/ITS4, respectively (sequences shown in FIG. 1A and given in reference [White, T. J., T. Bruns, S. Lee, and J. Taylor, 1990, "Amplification and direct sequencing of fungal ribosomal RNA genes for phylogenetics," in M. A. Innis, D. H. Gelfand, J. J. Sninsky, and T. J. White (ed.), *PCR Protocols, A Guide to Methods and Applications*, Academic Press, Inc., San Diego]). The parameters of the PCR reaction (35 cycles) were 94° C. for 1.5 min, 56 ° C for 1.5 min, and 72 ° C. for 1.5 min per cycle and a final extension cycle (10 min) at 72° C. Reaction mixtures (final volume 0.05 ml) contained: 250 µM of each dNTP, 0.5 µM of each primer, 1.25 units of Taq DNA polymerase, and 100 ng of DNA extracted from seeds, in 1× Taq DNA polymerase reaction buffer supplied by Pharmacia. The amplification products were resolved by electrophoresis in low melting agarose gels and purified from them using the QIAquick Gel Extraction Kit (Qiagen) or Agarase (Roche). The agarose electrophoresis analyses were performed on 1× TAE-3% agarose gels, and gels were stained with SYBR® Gold Nucleic Acid Gel Stain (Molecular Probes) and observed by UV illumination.

Figure 1B:
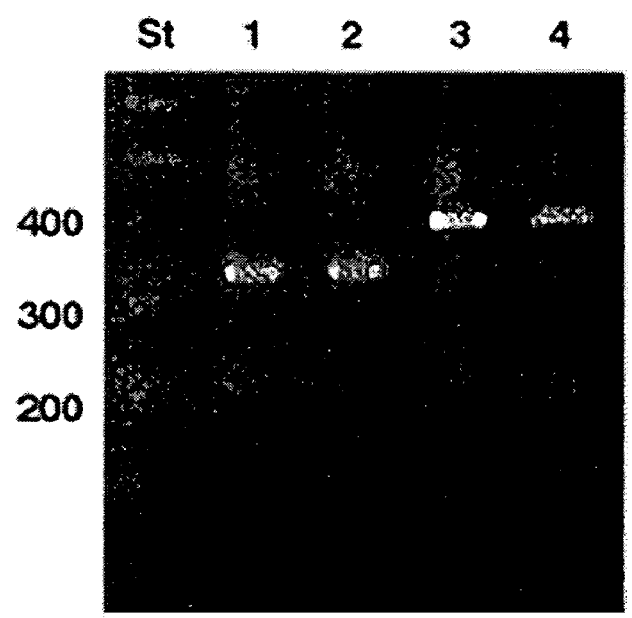
FIG. 1B shows the results of the electrophoretic analysis in agarose gels of the PCR amplicons from DNA extracted from guar and carob tree seeds. Samples were amplified by PCR using the primer pairs ITS5 (SEQ ID NO:1)/ITS2 (SEQ ID NO:5) (gel lanes 1 and 2) and ITS3 (SEQ ID NO:2)/ITS4 (SEQ ID NO:3) gel (lanes 3 and 4) and therefore contain the ITS1 region and the ITS2 region, respectively. Carob tree amplicons are in lanes 1 and 3, and guar amplicons correspond to lanes 2 and 4. Lane St corresponds to DNA molecular mass markers, whose sizes (in nucleotides) are indicated on the left side of the figure. Samples were detected by electrophoresis on agarose gels, staining with SYBR® Gold Nucleic Acid Gel Stain (Molecular Probes) and UV observation.

FIG. 1B shows the electrophoretic analysis of the amplification products obtained from the DNA extracted from the seeds of carob tree (odd lanes) and guar plant (even lanes). Amplicons shown on lanes 1 and 2 were obtained with the ITS5/ITS2 primers pair, thus resulting in amplification of the rDNA regions containing ITS1. Amplicons shown on lanes 3 and 4 were obtained with the primers pair ITS3/ITS4, thus resulting in amplification of the rDNA regions containing ITS2.

The products visualized in FIG. 1B were also sequenced on an Automated Applied Biosystems 373 DNA Sequencer using the fluorescent dye terminator procedure and the methods recommended by the supplier. Products were either directly sequenced or cloned in the pGEM®-T vector (Promega) and sequenced (in such cases, at least 3 clones of each amplification product were analyzed to establish the sequence). For sequencing, the following primers shown in FIG. 1A were used: ITS5 (SEQ ID NO:1) and ITS2 (SEQ ID NO:5), for sequencing the ITS1 products of FIG. 1B (lanes 1 and 2), and primers ITS3 (SEQ ID NO:2) and ITS4 (SEQ ID NO:3) for sequencing the ITS2 products of FIG. 1B (lanes 3 and 4).

FIGS. 2 and 3 show the resulting sequences aligned with the MacVector program. Sequence identifiers (sequence names) correspond to accession numbers given by the EMBL/GenBank/DDBJ DNA databases. The boundaries of the ITS sequences were determined by comparison of our sequences with those of other angiosperm plants [Hershkovitz, M. A., and E. A. Zimmer, 1996, "Conservation patterns in angiosperm rDNA ITS2 sequences," *Nucleic Acids Research*, 24:2857–2876]. As shown in FIGS. 2 and 3 there are several nucleotide positions in the aligned sequences that are different between the guar plant and carob tree sequences. Also, there are differences in the length of the sequences obtained from the two plant species: the ITS1 containing region of the guar plant is 2 nucleotides longer than that of the carob tree, and the ITS2 containing region of the carob tree sequence is 5 nucleotides longer than that of the guar plant. These differences in sequence length would suffice by themselves to distinguish if the amplification products originate from the guar plant or the carob tree, using methods that are known in the molecular biology field.

EXAMPLE II

Identification of Guar and Carob Tree by Amplification of DNA Extracted from their Seeds and Restriction Analysis of their ITS1 and ITS2 Regions.

Amplifications of the ITS1 and ITS2 containing regions from the DNA of the guar plant and carob tree seeds were obtained as detailed in the previous example. These PCR products were purified from other reaction components with the High Pure™ PCR Product Purification Kit (Boehringer). Purified amplicons were digested with the endonucleases detailed in FIGS. 4 and 5 using the conditions recommended by the endonucleases manufacturers (Pharmacia, Boehringer). The resulting restriction products were analyzed by electrophoresis in 1× TAE-4% agarose gels, and were detected and visualized as in previous electrophoretic analyses.

Figure 4:
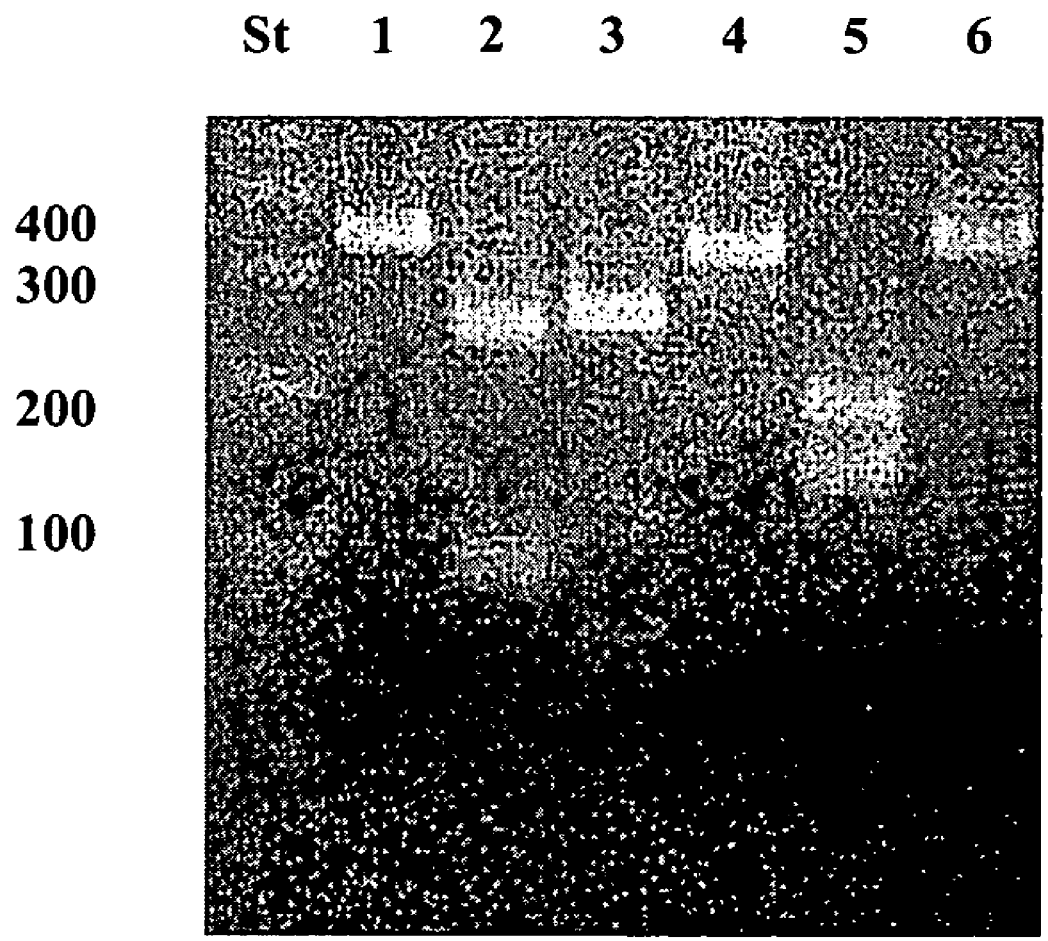
FIG. 4 shows an example of a restriction analysis of the ITS1 containing region of DNA extracted and amplified from the seeds of guar plant and carob tree. The ITS1 containing region was amplified by PCR with the ITS5/ITS2 primers pair and digested with endonucleases BcnI, ClaI, and HaeIII (lanes 1 and 2, 3 and 4, and 5 and 6, respectively). Odd lanes correspond to carob tree and even lanes to guar. Restriction products were detected as in FIG. 1B. Lane labeled St contains molecular mass markers, whose sizes (in nucleotides) are indicated on the figure left side.

FIG. 4 shows the results of the restriction analysis of the ITS1 containing regions amplified from the seeds of carob tree (odd lanes) and guar plant (even lanes), restricted with endonucleases BcnI (lanes 1 and 2), ClaI (lanes 3 and 4), and HaeIII (lanes 5 and 6). Clearly, as shown in the figure, this type of analysis could differentiate the guar DNA of this region from the same region of the carob tree DNA. For example, BcnI did not cut the carob tree DNA whereas this enzyme generates two fragments of 247 and 98 nucleotides in the guar sequence.

Figure 5:
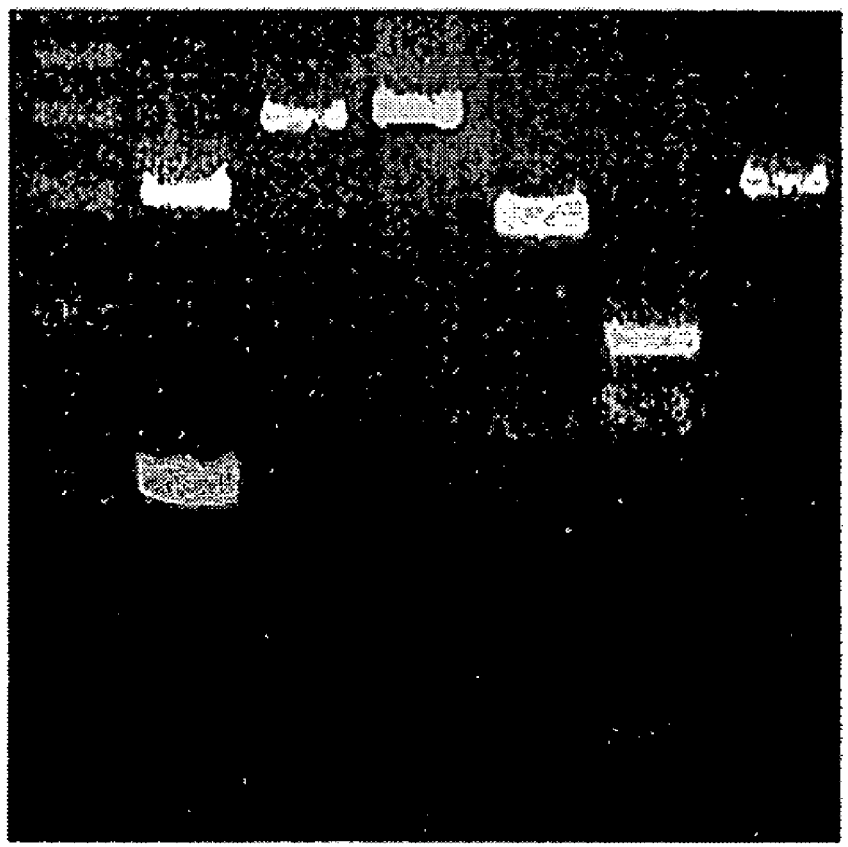
FIG. 5 shows an example of a restriction analysis of the ITS2 containing region of DNA extracted and amplified from the seeds of guar plant and carob tree. The ITS2 containing region was amplified by PCR with the ITS3/ITS4 primers pair and digested with endonucleases SmaI (lanes 1 and 2), XhoI (lanes 3 and 4), and HaeIII (lanes 5 and 6). Odd lanes correspond to carob tree and even lanes to guar. Restriction products were detected as in FIG. 1B. Lane labeled St contains molecular mass markers, whose sizes (in nucleotides) are indicated on the left side of the figure.

FIG. 5 shows the same type of analysis explained in the last paragraph but for the ITS2 containing regions. This Figure shows that, for example, the SmaI enzyme generates two fragments of 298 and 112 nucleotides from the carob tree DNA (lane 1), whereas no restriction was seen for the guar DNA (lane 2).

The examples shown in FIGS. 4 and 5 are non-limiting: using the same methodology but with other restrictases that are commercially available it would be possible to produce differential restriction patterns from the DNA of the two plants under study. In this type of restriction analyses, a prediction of the usefulness of the different endonucleases can be performed by computer-assisted restriction analysis of the sequences, using MacVector or other computer programs.

EXAMPLE III

Design and Use of PCR Primers Specific of the DNA Extracted from Guar Seeds

DNAs extracted from control seeds of guar and carob tree plants by the CTAB method (see example I) were amplified using primers PG21 (SEQ ID NO:4) and PG22 (SEQ ID NO:6) and the same PCR conditions detailed in example I, except that the annealing temperature was 55° C. The amplification products were detected by electrophoresis on 1× TAE-3% agarose gels, and visualized by ethidium bromide or SYBRO Gold staining and UV observation.

Figure 6:
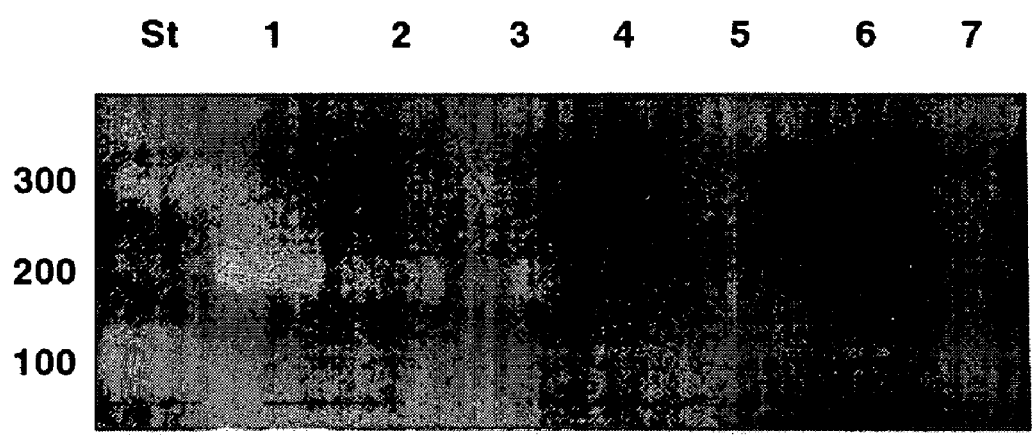
FIG. 6. Electrophoretic analysis of the PCR amplicons obtained with the PG21/PG22 primers pair from DNA extracted from the seeds of guar plant (lanes 1 to 3). DNA extracted from carob tree seeds was also tested for amplification using the same conditions and primers, but no amplification was detected (lanes 4 to 7). Amplicons were detected as in FIG. 1B. Lane St contains molecular mass markers, whose sizes (in nucleotides) are indicated on the left side.

FIG. 6 shows the results of this type of experiments, and demonstrates that primers PG21 (SEQ ID NO:4) and PG22 (SEQ ID NO:6) amplify specifically the DNA extracted from guar and not from carob tree. The amplification fragment should have a length of exactly 194 nucleotides, as deduced from sequence AJ245577 (SEQ ID NO:9, FIG. 3) in the region comprised between PG21 (SEQ ID NO:4) and PG22(SEQ ID NO:6). As shown in FIG. 6, the fragment amplified from different guar seeds runs in the gels slightly below the 200 nucleotides marker, i.e., with the expected molecular mass.

EXAMPLE IV

Extraction of DNA from Guar and Locust Bean Gums and their Mixtures

DNA extraction from guar and locust bean gum and their mixtures was performed as follows. Ten mg of gums, obtained as powders from the suppliers, were suspended in 10 ml of either water (water method), 10 mM Tris-HCl pH 8.5 (Tris method), water: acetonitrile 7:3 (acetonitrile method), or 35% ethanol (ethanol method). Suspensions were vortexed for 5 min and centrifuged for 1 min at 15,000×g. Supernatant fluids were recovered and used for PCR and quantitation assays, except in the ethanol method, where the procedure explained in the reference [Michaels, S. D., M. C. John, and R. M. Amasino, 1994, "Removal of polysaccharides from plant DNA by ethanol precipitation," *Biotechniques*, 17:274–276] was followed, and the final pellet obtained by this method was dissolved in 0.5 ml of water. For quantitation assays of the DNA extracted by the above four methods, 0.1 ml samples for DNA and the PicoGreen[R] dsDNA Quantitation Kit of Molecular Probes were used. For total sugars quantitation, 0.01 ml of samples (extracts) and the phenol-sulfuric acid method [Keleti, G., and W. H. Lederer, 1974, *Handbook of Micromethods in the Biological Sciences*, Van Nostrand Reinhold, New York] were used. For PCR amplification, 0.005 ml of extracts were amplified with the PG21 (SEQ ID NO:4)/PG22 (SEQ ID NO:6) primers pair and the conditions described in Example III. The results obtained with these extraction methods are summarized in Table 1.

TABLE 1

Specific detection of guar gum, alone and in guar/locust bean gum mixtures, by PCR amplification of the DNA extracted from the gums. Dependence of the detection on the method used for DNA extraction.

| Gums | Extraction method | DNA[1] | Hexoses[2] | DNA/ polysaccharide | PCR[3] |
|---|---|---|---|---|---|
| Guar | H$_2$O | 46.87 | 0.639 | 1/14,000 | + |
| 30% Guar[4] | H$_2$O | 8.6 | 0.523 | 1/60,000 | + |
| 10% Guar[4] | H$_2$O | 10.8 | 0.541 | 1/50,000 | + |
| Locust bean | H$_2$O | 14.22 | 0.572 | 1/40,000 | − |
| Guar | Tris | 77.3 | 1.056 | 1/14,000 | + |
| 0% Guar[4] | Tris | 156.1 | 0.361 | 1/2,500 | − |
| 10% Guar[4] | Tris | 232.5 | 0.494 | 1/2,000 | − |
| Locust bean | Tris | 509.7 | 0.721 | 1/1,500 | − |
| Guar | Acetonitrile | 4.84 | 0.013 | 1/3,000 | + |
| 30% Guar[4] | Acetonitrile | 1.72 | 0.019 | 1/11,000 | − |
| 10% Guar[4] | Acetonitrile | 1.94 | 0.030 | 1/16,000 | − |
| Locust bean | Acetonitrile | 1.72 | 0.029 | 1/17,000 | − |
| Guar | Ethanol | 3.21 | ND[5] | NA[6] | − |
| 30% Guar[4] | Ethanol | 0.3 | ND | NA | − |
| 10% Guar[4] | Ethanol | 0.64 | ND | NA | − |
| Locust bean | Ethanol | 0.86 | ND | NA | − |

[1]In ng/ml. Quantitated with the PicoGreen[R] dsDNA Quantitation Kit of Molecular Probes.
[2]In mg of dissolved polysaccharide detected using the phenol-sulfuric method [Keleti, G., and W. H. Lederer, 1974, Handbook of Micromethods in the Biological Sciences Van Nostrand Reinhold, New York.] per mg of gum.
[3]Amplification (+) or no amplification (−) by PCR using the PG21/PG22 primers pair and detection as in FIG. 1B.
[4]Percent (w/w) guar in the locust bean gum-guar gum mixtures.
[5]Not detected.
[6]Not applicable.

As shown in Table 1, the four assayed methods had different efficiencies in extracting the DNA from guar gum and locust bean gum. Clearly, the Tris method was the most efficient one, followed by the water, acetonitrile, and the ethanol methods. These efficiencies in DNA extraction do not always correlate with the amount of solubilized polysaccharide, as can be deduced from the Table column showing the DNA to polysaccharide ratios obtained for each solubilization method. When extracting individual gums (100% guar or locust bean gum), it is clear that the Tris method is, compared to the other methods, much more efficient for the extraction of DNA from locust bean gum than from guar gum. This can be deduced from the ratios of DNA extracted by each method from each gum: for locust bean gum, the amount of DNA extracted by Tris divided by the amount of DNA extracted by water is 35.8, whereas the same ratio for guar gum is 1.6.

The above results help to understand the results found when DNA extraction methods were assayed on locust bean gum with known additions (30% or 10%, w/w) of guar gum, and the results obtained when the DNAs extracted from the gums and their mixtures were assayed by PCR. Clearly, although the water method extracts less DNA than the Tris method from each gum or mixture assayed, the water method is the most adequate for detecting guar DNA extracted from guar gum or guar/locust bean gum mixtures. This is demonstrated in column labeled as "PCR" in Table 1, where the results of PCR amplification with the guar specific primers PG21 (SEQ ID NO:4)/PG22 (SEQ ID NO:6) are shown. Clearly, although the Tris method extracts more DNA than the water method from locust bean gum containing 30% or 10% guar gum, only the water method results in positive amplification and detection of the guar DNA contained in these mixtures. These extraction and PCR results suggest that most of the DNA extracted from gums mixtures using the Tris solvent should actually correspond to locust bean DNA, rather than guar DNA, whereas with the water method sufficient guar DNA is extracted from guar/locust bean gum mixtures to allow its PCR amplification with the guar specific primers PG21 (SEQ ID NO:4)/PG22 (SEQ ID NO:6).

In summary, the results obtained advised to use the water method for the detection of guar gum in mixtures of guar gum and locust bean gum by the PCR methods described in this patent.

EXAMPLE V

Specific Detection of Guar DNA in Guar Gum and in Mixtures of Guar Gum and Locust Bean Gum In this example, laboratory preparations of locust bean gum containing different known amounts of guar gum and commercial locust bean gum samples were tested. DNA extraction by the water method described in the previous example and PCR amplifications with the PG21 (SEQ ID NO:4)/PG22 (SEQ ID NO:6) primers described in previous examples were used. Results of these studies are shown in FIGS. 7 and 8.

Figure 7:
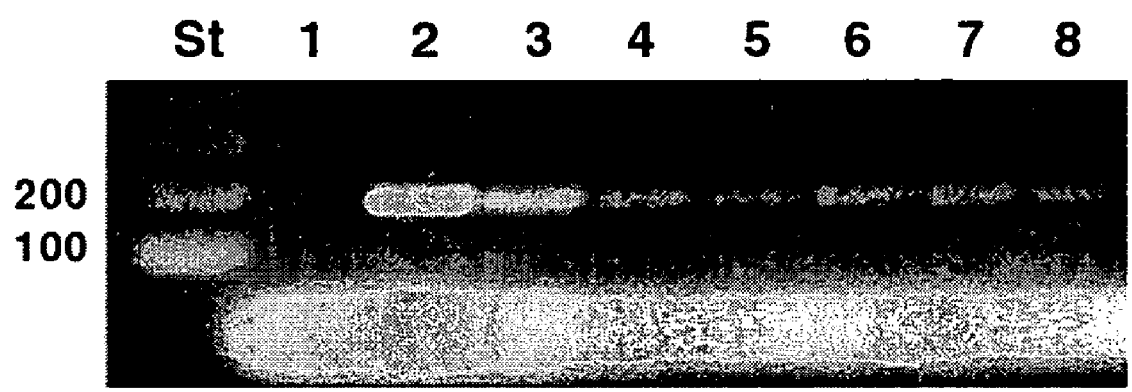
FIG. 7. Electrophoretic analysis of the PCR amplification products of DNA extracted from guar and locust bean gums and mixtures of both gums. DNA was extracted by the water method and amplified using the PG21/PG22 primers pair. Lanes 1 and 2 show the amplicons from negative and positive control samples, locust bean gum (lane 1) and guar gum (lane 2), respectively. Lanes 3, 4, and 5 show the amplicons obtained from locust bean gum samples containing 30%, 20%, and 10% guar gum, respectively. Lanes 6, 7, and 8 show the amplicons obtained from locust bean gum samples containing 12%, 6%, and 2% guar gum, respectively. The locust bean gum analyzed in lane 1 was used for making all the gum mixtures. Mixtures on lanes 3 through 5 were prepared with the guar gum sample shown on lane 2, and mixtures on lanes 6 through 8 were prepared with a different guar gum source.
Figure 8:
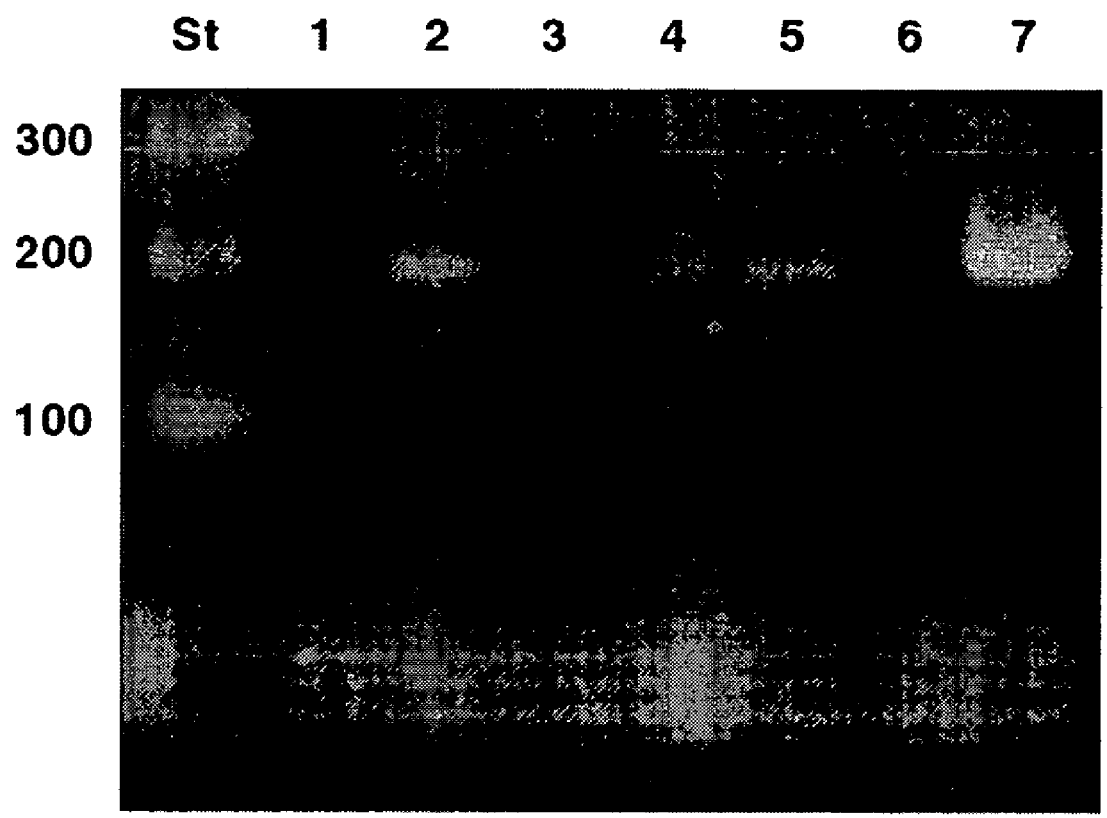
FIG. 8. Electrophoretic analysis of the amplicons obtained from different commercial samples and providers and labeled as "locust bean gum". DNA was extracted from these samples using the water method and amplified by PCR with the PG21/PG22 primers pair. Lanes contained amplicons from the commercial samples of locust bean gum (1 through 5), a negative control (locust bean gum, lane 6) and a positive control (guar gum, lane 7).

FIG. 7 shows the results of testing laboratory mixtures of locust bean containing 30%, 20% and 10% of guar gum. These three mixtures were prepared from the same two samples of locust bean gum and guar gum. Reasoning that perhaps different gum manufactures may produce guar gums with different amounts of DNA, depending on their production processes or other reasons, we also prepared mixtures of the same locust bean gum plus a different guar gum. These locust bean gum mixtures contained 12%, 6% and 2% guar gum. As shown in FIG. 7, all the locust bean gum mixtures containing guar gum produced by PCR with the PG21 (SEQ ID NO:4)/PG22 (SEQ ID NO:6) primers an amplification band of the expected size, independently of the amount of guar present in the mixture. Control samples containing only locust bean gum or only guar gum gave the expected results: negative (no amplification by PCR) for the locust bean gum and positive (PCR amplification) for the guar gum. It is worth noting that, confirming our expectations, different commercial samples of guar gum contain different amounts of DNA. This can be deduced from the comparison of the results obtained, for example, from mixtures containing 2% and 10% guar gum (FIG. 7 lanes 8 and 5, respectively). These two samples were prepared with the same locust bean gum but with guar gums from two different providers.

The usefulness of the methods described here for detecting guar gum was also tested on commercial preparations labeled as "locust bean gum". We obtained these commercial samples from different providers and selected some of them for study following the methods described in this patent. Particularly, we selected those samples producing viscosities higher than 250 cps at room temperature, since locust bean gum at this temperature usually produces viscosities not higher than 100 cps, and higher viscosities could be due to oversight or undeclared presence of guar gum. As shown in FIG. 8, four out of the four theoretically pure locust bean gum preparations studied produced positive amplifications by PCR with the guar-specific primers pair PG21 (SEQ ID NO:4)/PG22 (SEQ ID NO:6) (lanes 2 through 5 in this Figure). This indicates that the four mentioned samples contained guar, although in different proportions, as can be deduced from the different intensities of the gel bands (compare for example lanes 2 and 3). Control gums produced the expected results: locust bean gum produced no amplification (lane 6), whereas guar gum amplified (lane 7). One commercial sample labeled as "locust bean gum" with the usual viscosity values of locust bean gum was also negative by PCR (lane 1).

Figure 9:
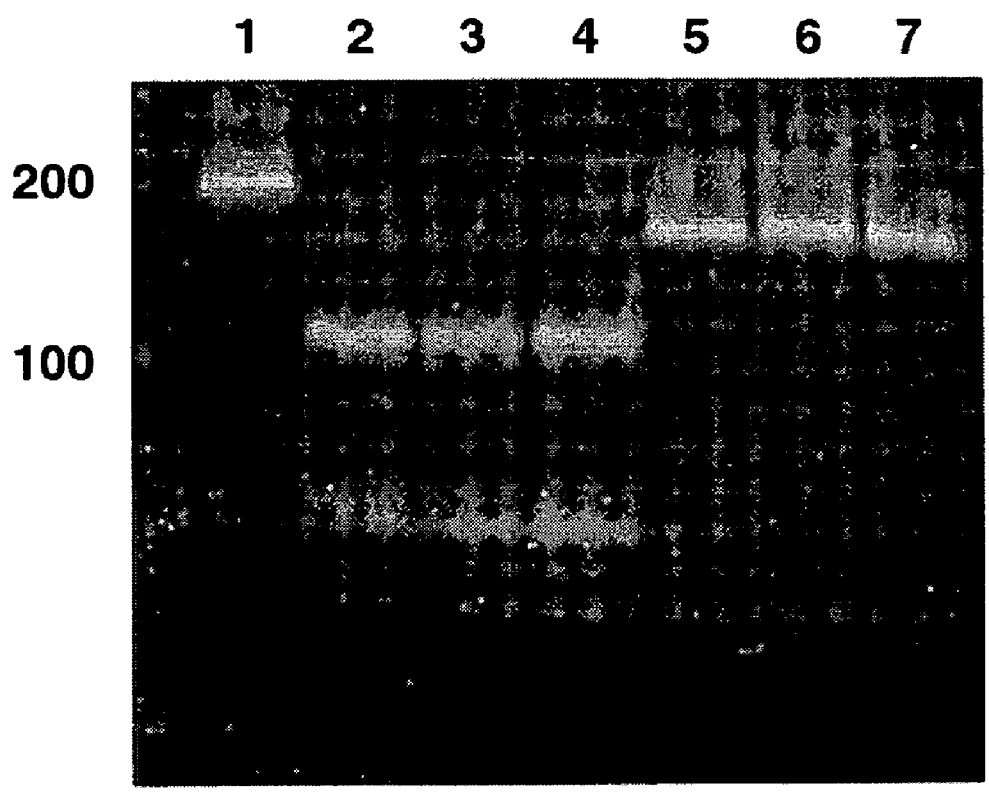
FIG. 9. Restriction analysis of the amplification products shown in FIG. 8 restricted with the TaqI (lanes 2 through 4) and XhoI (lanes 5 through 7) enzymes. Lanes 2 and 5, 3 and 6, and 4 and 7, contain respectively the amplification products of lanes 2, 5, and 7 of FIG. 8. Lane 1 shows the unrestricted amplicon from FIG. 8 lane 7 (control guar amplicon).

An additional proof of the guar presence in some commercial preparations labeled as "locust bean gum" was obtained by restriction analysis of the amplification products mentioned in the last paragraph. For designing this analysis, we followed the directions and methods used in Example II and the AJ245577 (SEQ ID NO:9) sequence shown in FIG. 3. As shown in FIG. 9, the amplification products seen in FIG. 8 contained two restriction sites for endonuclease TaqI, which generates three fragments of 106, 52, and 36 nucleotides. The same enzyme would generate (as shown by computer-assisted restriction analysis) only two fragments of 143 and 52 nucleotides on the equivalent carob tree sequence, i.e., the sequence comprised between the PG21 (SEQ ID NO:4) and PG22 (SEQ ID NO:6) primers. Additionally, the XhoI enzyme, which does not cut the carob tree sequence, produces two fragments in the amplicons, as expected from the guar sequence comprised between PG21 (SEQ ID NO:4) and PG22 (SEQ ID NO:6) sequences. Thus, the enzymes used in this example are diagnostic, but also other enzymes (as discussed in Example II) can be used for the same purpose.

The invention claimed is:

1. A method for obtaining and amplifying extracted DNA from gum samples comprising one or more of guar gum (E 412) and locust bean gum (E 410), comprising the steps of:
   i) contacting a gum sample comprising DNA and one or more of guar gum (E 412) and locust bean gum (E 410) with an aqueous solution to form an extraction mixture;
   ii) agitating the extraction mixture at a temperature between 0° C. and 100° C. for a time period sufficient to permit extraction of DNA from the gum sample into the aqueous solution;
   iii) separating the extraction mixture to obtain an aqueous solution containing extracted DNA and another phase;
   iv) recovering a sample of the aqueous solution containing extracted DNA; and
   v) using PCR to amplify the extracted DNA using one or more primers having a sequence of SEQ ID NO:5, SEQ ID NO:6.

2. The method according to claim 1 wherein said aqueous solution is a buffered aqueous solution.

3. The method according to claim 1 wherein said aqueous solution further comprises acetonitrile or ethanol.

4. The method according to claim 1 wherein the extraction mixture is agitated at room temperature.

5. The method according to claim 1 wherein the extraction mixture is separated by decantation.

6. The method according to claim 1 wherein the extraction mixture is separated by centrifugation.

7. The method according to claim 6 wherein the centrifugation is at 15,000×g.

* * * * *